US006264626B1

(12) United States Patent
Linares et al.

(10) Patent No.: US 6,264,626 B1
(45) Date of Patent: Jul. 24, 2001

(54) PAPERBOARD APPLICATORS HAVING IMPROVED GRIPPING FEATURES

(75) Inventors: Carlos G. Linares, Mountainside; Linda M. Pierson, Somerville, both of NJ (US)

(73) Assignee: McNeil-PPC, Inc., Skillman, NJ (US)

( * ) Notice: Subject to any disclaimer, the term of this patent is extended or adjusted under 35 U.S.C. 154(b) by 0 days.

(21) Appl. No.: 09/340,099

(22) Filed: Jun. 25, 1999

(51) Int. Cl.$^7$ .................................................. A61F 13/20
(52) U.S. Cl. ............................................................ 604/15
(58) Field of Search .............................. 604/11–18, 904, 604/57–60, 285, 286, 311

(56) References Cited

U.S. PATENT DOCUMENTS

| | | | |
|---|---|---|---|
| 2,751,907 | * | 6/1956 | Hickey ................................ 604/57 |
| 3,086,527 | * | 4/1963 | Forrest ................................ 604/11 |
| 3,757,781 | * | 9/1973 | Smart ................................... 604/57 |
| 3,831,605 | | 8/1974 | Fournier . |
| 3,921,632 | * | 11/1975 | Bardani ............................... 604/57 |
| 4,060,083 | * | 11/1977 | Hanson ............................... 128/223 |
| 4,361,150 | | 11/1982 | Voss . |
| 4,428,370 | * | 1/1984 | Keely ................................... 128/127 |
| 4,447,222 | | 5/1984 | Sartinoranont . |
| 4,508,531 | | 4/1985 | Whitehead . |
| 4,536,178 | * | 8/1985 | Lichstein et al. .................. 604/15 |
| 4,573,963 | * | 3/1986 | Sheldon ............................... 604/15 |
| 4,573,964 | | 3/1986 | Huffman . |
| 4,755,164 | | 7/1988 | Hinzmann . |
| 4,822,332 | * | 4/1989 | Kajander ............................. 604/16 |
| 4,921,474 | | 5/1990 | Suzuki et al. . |
| 5,330,421 | | 7/1994 | Tarr et al. . |
| 5,346,468 | | 9/1994 | Campion et al. . |
| 5,348,534 | * | 9/1994 | Tomaszewski et al. ............ 604/14 |
| 5,709,652 | | 1/1998 | Hagerty . |
| 5,782,793 | | 7/1998 | Nielsen et al. . |
| 5,788,663 | * | 8/1998 | Igaue et al. ......................... 604/15 |
| 5,800,377 | | 9/1998 | Campion et al. . |
| 5,823,988 | | 10/1998 | Orenga et al. . |
| 5,827,214 | | 10/1998 | Fox et al. . |

FOREIGN PATENT DOCUMENTS

| | | |
|---|---|---|
| 0 418 791 | 3/1994 | (EP) . |
| 0 966941 A2 | 12/1999 | (EP) . |
| 2 166 656A | 5/1986 | (GB) . |

* cited by examiner

Primary Examiner—Dennis Ruhl

(57) ABSTRACT

The present invention relates to applicators comprising an elongate insertion member having an insertion end and a gripper end opposite thereof, wherein the gripper end has an indentation with a shoulder on each end of the indentation. The shoulder most proximal the insertion end provides resistance to finger slip during the step of inserting the applicator into a body cavity. Whereas the shoulder most proximal the gripper end provides resistance to finger slip during the step of expelling material substantially contained by the applicator. The shoulder most proximal the gripper end also provides secure handling of the applicator while removing the applicator from the body after the expulsion step has been completed.

20 Claims, 2 Drawing Sheets

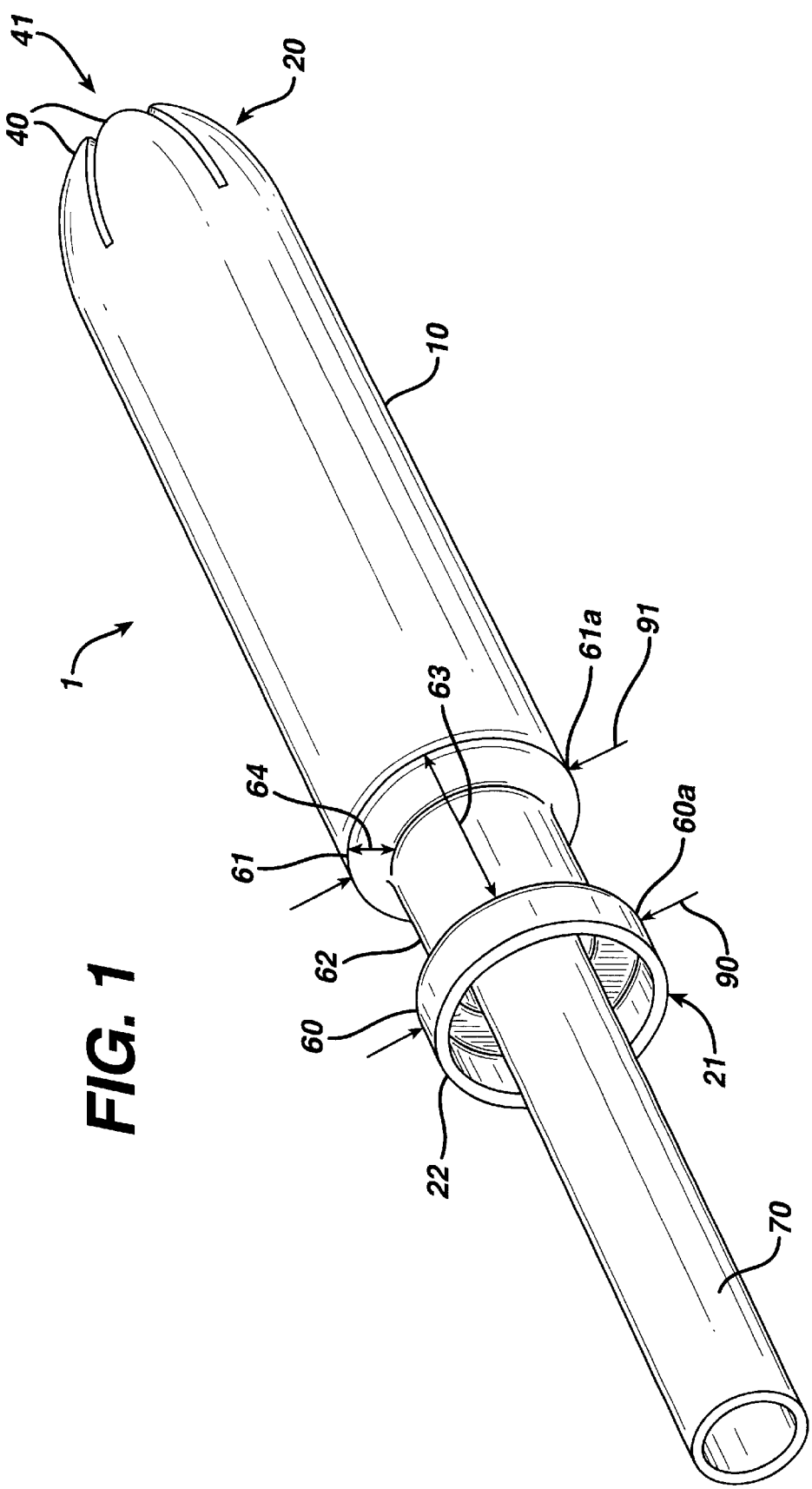

PAPERBOARD APPLICATORS HAVING IMPROVED GRIPPING FEATURES

CROSS-REFERENCE TO RELATED APPLICATIONS

This invention is related to the following copending application: U.S. Ser. No. 09/340,312, filed Jun. 25, 1999, entitled "A Method of Making Applicators having Improved Grip Features" (Att'y Docket, PPC-705).

FIELD OF THE INVENTION

The present invention relates to paperboard applicators for delivering materials into mammalian body cavities having an indentation in a finger grip region with shoulders on each end of the indentation. The applicator is particularly useful for delivering catemenial devices into a vaginal canal.

BACKGROUND OF THE INVENTION

Applicators for delivering materials into a body cavity typically comprise a tubular insertion member having an insertion end and a gripper end opposite thereof, and an elongate expulsion member slideably fitted within the tubular insertion member for expelling the contained materials. The gripper end will generally incorporate features to allow a user to more or less securely hold the applicator during use, which includes the following steps: inserting the applicator into a body cavity, expelling a substantially enclosed material contained by the applicator, and withdrawing the applicator from the body.

Over the years, attempts have been made to improve the gripping features. One approach is to significantly reduce the diameter of the applicator in the gripper end, as can be seen in the following U.S. Pat. Nos.: 4,508,531; 4,573,963; 4,755,164; and 4,573,964. For example, Whitehead (U.S. Pat. No. 4,508,531) discloses providing a blank with a plurality of slightly recessed areas outlined by scored lines, which result in a reduced diameter gripping portion when the blank is formed into a tubular structure. Whitehead discloses that the reduced diameter is for positioning and gripping a tube prior to insertion. While a reduced diameter grip may help in preventing fingers from slipping during insertion, there is little or no resistance offered in the opposite direction during the expulsion step. This is a step with which many users have difficulty.

Another approach to improve the grip of the applicator during use is to incorporate projections, such as in the form of a ring, at the base of the applicator member being inserted into the body. Examples of this approach are disclosed in Voss, U.S. Pat. No. 4,361,150, and Sartinoranont, U.S. Pat. No. 4,447,222. Similar to the disadvantage of applicators employing a reduced diameter in the gripper end, projections typically provide only a single direction of resistance. In most cases, the resistance provided is intended to aid during the expulsion step.

A number of attempts have been made to provide dual direction resistance to finger slip. Suzuki et al., U.S. Pat. No. 4,921,474, discloses a plastic applicator having a shoulder and an annular rib spaced therefrom in a region adjacent its rear end for gripping the applicator. The drawings in '474 depict the annular rib having a smaller height dimension than that of the shoulder, resulting in decreased resistance to finger slip during a step of expelling a tampon. Forces required to expel materials from an applicator can be as great, or greater, than the forces required to place the insertion member into a body cavity, thereby necessitating the need for as great of resistance for the fingers in directions away from the insertion end as that towards the insertion end. Additionally, it is relatively easy to employ gripping features in a plastic applicator due to the inherent formability of thermoplastic materials.

Most paperboard applicators have gripping features that provide limited resistance to finger slip during use. One example of this, Hagerty, U.S. Pat. No. 5,709,652, discloses an applicator having a plurality of finger-accepting apertures to provide relatively abrupt, finger-accepting edges to frictionally resist movement of a user's finger in response to longitudinal forces on the device. Although a useful contribution to the art, the finger-accepting edges of Hagerty are limited to the wall thickness of the tubular element. The width of the finger-accepting apertures is also limiting, in that only a portion of a user's finger will fit between the edges.

Another example, Tarr et al., U.S. Pat. No. 5,330,421, discloses a tampon applicator having relatively shallow indentations at the distal end. In addition to the indentations being shallow, they are depicted as being relatively narrow, resulting in the potential of bridging the indentation with a finger. If bridging occurs, then little or no resistance is offered by the indentations.

Thus, a need still exists for a paperboard applicator having gripping features that provide significant resistance to finger slip in two directions, as needed during insertion of the applicator into a body cavity and expulsion of materials substantially contained by the applicator.

SUMMARY OF THE INVENTION

The present invention relates to a paperboard applicator for delivering materials contained therein into a mammalian body cavity. The applicator includes an elongate paperboard insertion member having an insertion end and a gripper end opposite thereof. The gripper end has an indentation dimensioned to substantially accept a user's manual digit defined by a first shoulder substantially adjacent the gripper end and a second shoulder disposed toward the insertion end.

Such applicators are useful for the delivery of catemenial devices, such as tampons, intravaginal collection devices, and interlabial pads. The applicators are also useful for delivery of oral, rectal, and vaginal suppositories, as well as nasal devices, such as nasal tampons. Further, it can be used for delivery of various other materials including, medicaments, moisturizers, vitamins and minerals, spermicides, and odor controlling agents. These materials may be in the form of solids, creams, foams, gels, and the like.

BRIEF DESCRIPTION OF THE DRAWINGS

FIG. 1 is a perspective view of a paperboard applicator provided by the present invention comprising an indention in the gripper end, with two shoulders on each end of the indentation.

DETAILED DESCRIPTION OF THE INVENTION

Figure 2A:
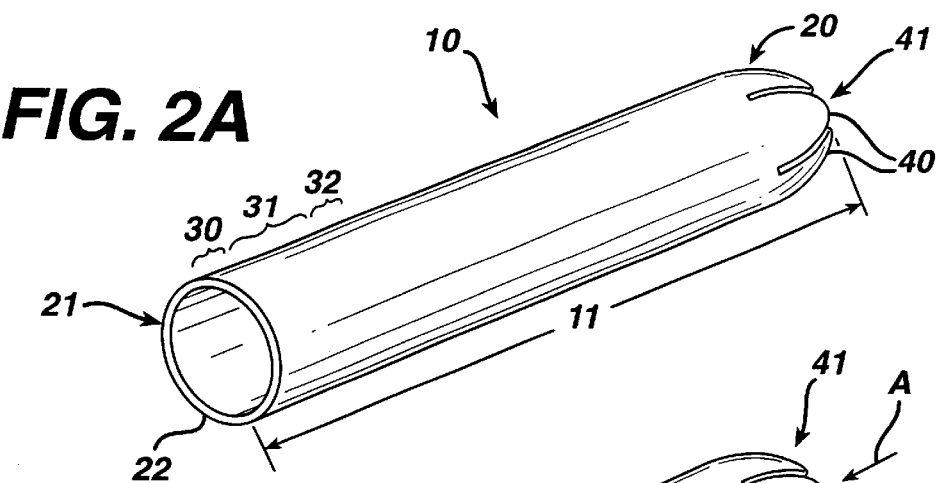
FIGS. 2A–2D depict steps (including optional steps) in a method of making the applicator of FIG. 1.

The present invention relates to paperboard applicators for delivering materials into body cavities, comprising elongate insertion members that are intended to be at least partially inserted into a body cavity. The elongate insertion members have an insertion end and gripper end opposite thereof. To improve a user's ability to securely hold the applicator during use, the gripper end of the insertion member employs an indentation with shoulders on each end of the indentation.

Referring now to the drawings, wherein like reference numerals designate like elements, FIG. 1 depicts an applicator 1, comprising a tubular insertion member 10, having a length 11 (shown in FIG. 2) that runs from an insertion end 20 to a gripper end 21. The insertion end may have a plurality of inwardly curved petals 40 that form a substantially closed dome 41. The gripper end 21 comprises an indentation 62 having a length 63, a depth 64, a first shoulder 60 and a second shoulder 61 located on either end of the indentation 62.

It is important for the length 63 to be of sufficient dimension to substantially accept a user's manual digit (width) within the confines of both of the shoulders 60 and 61. If a user's manual digit does not substantially fit within the indentation, then excess bridging of one or more of the shoulders may occur, substantially compromising the benefits provided by the indentation and shoulders, as described in detail below. As used in the specification and claims, the term "manual digit" means any of the digits extending from a hand, e.g. a thumb or finger. Length 63 is preferably at least 10 millimeters, more preferably from about 10 to about 25 millimeters, and most preferably from about 15 to about 20 millimeters. The depth 64 of the indentation is preferably from about 0.5 to about 3.5 millimeters and more preferably from about 1 to about 2.5 millimeters.

The indentation length 63 and depth 64 both provide for secure handling of the tubular insertion member 10. It is preferable to employ an indentation 62 having a length 63 of at least 10 millimeters and a length:depth ratio from about 4:1 to about 25:1.

When a user inserts the tubular insertion member 10 into a body cavity, her fingers and/or thumb are urged towards the insertion end 20 due to the frictional forces between the insertion member 10 and the walls of the body cavity. Shoulder 61 provides resistance to this movement, thereby providing a secure hold. Once the tubular insertion member 10 is successfully inserted into the body, a user can then expel material contained by the applicator. This is typically performed by displacing an elongate expulsion member, shown as element 70, into the tubular insertion member 10. During the expulsion step, her fingers and/or thumb are urged towards the gripper edge 22 due to the potential combination of many factors, such as the frictional forces between insertable material (not shown) and the inner wall of the tubular insertion member 10, and the forces required to open the substantially closed dome 41. Shoulder 60 provides resistance to this particular movement. The indentation 62 itself also provides improved handling of the applicator, because its reduced diameter increases the percentage of surface area contacted by a user's manual digits.

Preferably, the indentation 62 has a perimeter that is from about 60 to about 90% of a first perimeter 90 and a second perimeter 91 defined by the two shoulders 60 and 61, and more preferably from about 70 to about 80%. The first and second perimeters 90 and 91 are measured from apex points 60a and 61a, which are terminal shoulder points most distal the indentation 62. Preferably, the first and second perimeters 90 and 91 are dimensionally equal. However, they may also be different. Further to the benefit of relative difference in perimeter between the indentation 62 and the two shoulders 60 and 61, is the degree of transition from apex points 60a and 61a to the indentation 62. The resistance provided by the shoulders 60 and 61 increases as their effective radius decreases (i.e. as the transition approaches 90°). As used herein in the specification and claims, the term "perimeter" relates to the measurement about the structure as measured in and defined by a plane perpendicular to the longitudinal axis of the blank or the insertion member. This measurement may be on the inside or the outside of the structure. The perimeter of a substantially tubular structure is related to its diameter.

The applicator of the present invention can be made by manipulating a pre-made insertion member through a series of steps as can be seen in FIGS. 2A–2D. FIG. 2A depicts a pre-made tubular insertion member 10, having a length 11, an insertion end 20, a gripper end 21 opposite thereof, and optionally a plurality of inwardly curved petals 40 to form a substantially closed dome 41. The gripper end 21 comprises a gripper edge 22 and three adjacent regions: first region 30, second region 31, and third region 32. The second region 31 should be of sufficient length to substantially accept an ordinary person's finger or thumb. First region 30 and third region 32 are preferably much shorter in length compared to the second region 31.

Figure 2B:
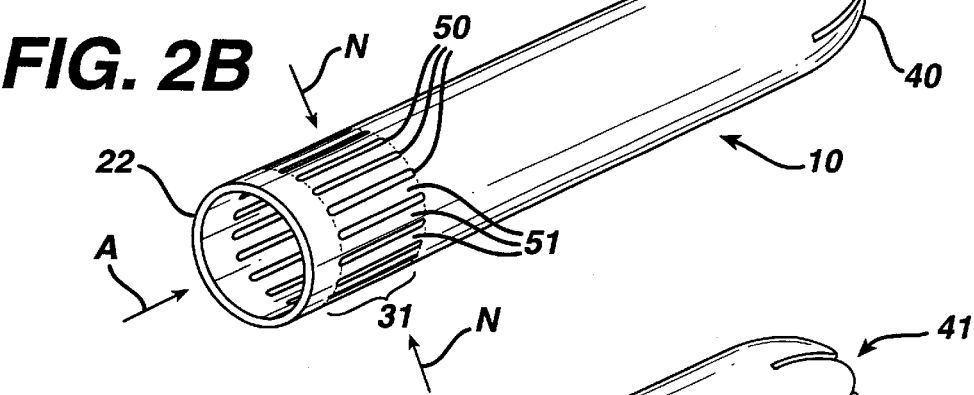

A plurality of discrete sections 50 are removed from the second region 31, while maintaining non-removed sections 51, as shown in FIG. 2B. A representative, non-limiting list of methods useful for removing the sections 50 is the following: die-cutting, laser cutting, water jet cutting, thermoforming, grinding, and the like. The removed sections 50 have a major axis and a minor axis, with the major axis preferably oriented substantially parallel to the length 11 of the tubular insertion member 10. Alternatively, the major axis may be oriented at an acute angle to the length 11 of the tubular insertion member 10. The removed sections 50 have a length dimension that is parallel to the major axis from about 40 to about 90 millimeters, and a length dimensions that is parallel to the minor axis from about 0.2 to about 1.5 millimeters. The length dimensions may be constant or varying along the periphery of the removed sections 50.

Figure 2C:
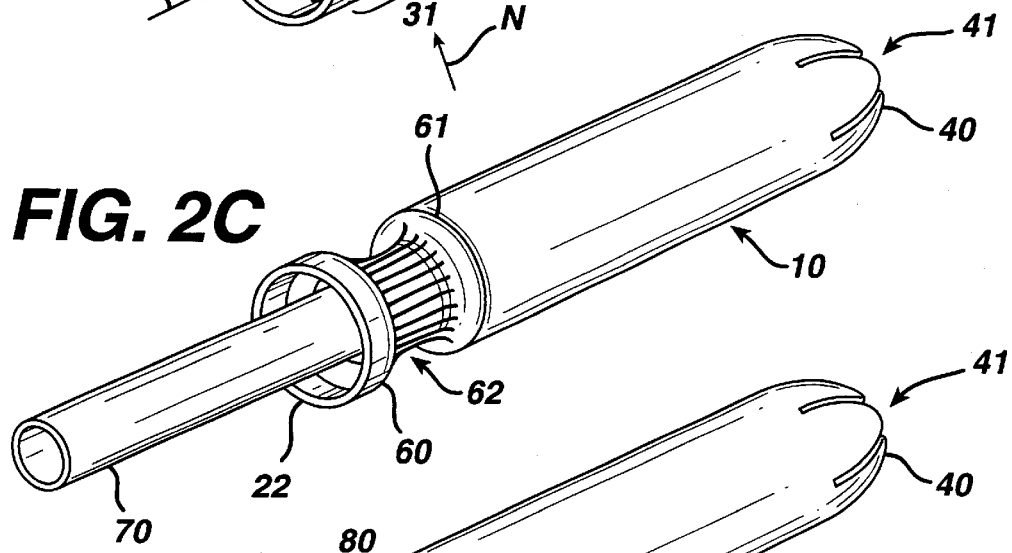

Referring to FIG. 2C, after removing the discrete sections 50, the second region 31 is collapsed to a diameter less than the diameter of the first region 30 and the third region 32. By collapsing the second region 31, an indentation 62 defined by shoulders 60 and 61 at the interface of the second region 31 and each of the first region 30 and third region 32, respectively. These shoulders 60 and 61 collectively provide resistance to finger/thumb slip in two directions. Applying a normal force N to the second region 31, or applying a combined axial force A to the tubular insertion member 10 and a normal force N to the second region 31 can collapse the second region 31, as shown in FIG. 2B.

The collective amount of material removed in the second region will generally dictate the difference in diameter between the collapsed second region and the first and third regions. Preferably, the diameter of the collapsed second region is from about 60% to about 90% of the diameter of the first and third regions.

Figure 2D:
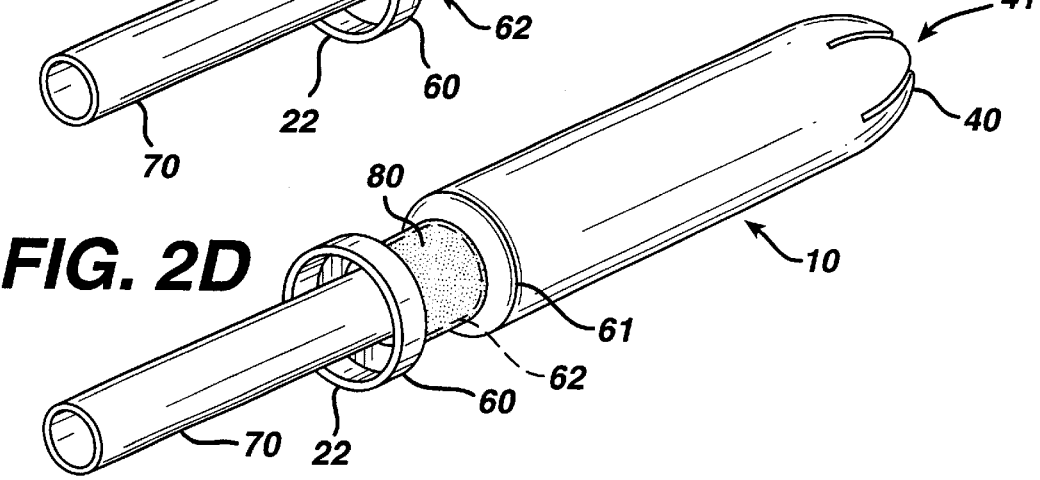

As shown in FIG. 2D, optional materials may be added to the finger gripping region for a variety of reasons. These materials may be added as an indicator for where a user should grasp the applicator, as an indicator for differentiating products such as different absorbency tampons, and the like. Additionally, materials may be added within the indentation to further increase resistance to finger slip through increased friction, or to maintain the indentation once it is formed, thereby minimizing the tendency for the indentation to "spring back." Preferred materials are elastomers 80, such as rubber; other polymeric materials, such as those that are shrinkable upon exposure to sufficient energy; and pigments or dyes.

While FIGS. 2A–2D depict making an applicator comprising an indentation starting from a pre-made tubular structure, similar methods can be utilized by starting with a sheet of material, wherein sections are removed in the sheet and then forming the sheet around a mandrel into the shape of a tube. The indentation may be post-formed after the tubular structure is made, or formed simultaneously with the forming of the tubular structure by utilizing a mandrel having a corresponding indentation.

Alternative methods for making applicators of the present invention include the following: papier-mache techniques and other paper laminating techniques, folding paperboard members to form pleats in the gripper region with or without the use of added plasticizers, and the like. More generally, there are a number of processes for making tubular paperboard applicators known in the art, as described herein below.

Paperboard applicators can be constructed from a single layer of paperboard material, or from a plurality of laminated layers to provide multiple benefits relating to the various layers. Useful paperboard stock for the formation of the tubular insertion members and expulsion members include, without limitation, cardboard, paperboard, cup stock, paper, laminated wood chips, and the like. The applicators can be made by the following non-limiting processes: spiral winding as disclosed in U.S. Pat. No. 5,346,468, convolute winding as disclosed in U.S. Pat. No. 4,508,531, and forming a sheet around a mandrel and then sealing an overlapped seam as disclosed in U.S. Pat. No. 4,755,164.

The paperboard applicators may include a surface layer, which may be useful to increase the comfort and ease of insertion and withdrawal of the applicator. The surface layer may be in the form of laminated films, coatings, and the like. An example of such a surface layer is disclosed in Blanchard, co-pending application U.S. Ser. No. 09/105,787 filed on Jun. 26, 1998. A representative, non-limiting list of useful materials to be used as the surface layer includes, waxes, cellophane, polyolefins, polyesters, epoxies, and the like. The surface layers may also include thermal stabilizers, pigments, fragrances, surfactants, antimicrobial agents, medicaments, and the like. There are many techniques known for applying the surface layers. A representative, non-limiting list of such techniques includes spraying, extruding, slot-coating, brushing, transfer coating, and the like. Additional processing steps may be required to cure the surface treatments to a useable form other than simple air curing, such as applying irradiation or other forms of energy.

Typical dimensions for each of the tubular insertion and expulsion members include a length of from about 50 to about 100 millimeters, a diameter of from about 8 to about 16 millimeters, and a thickness of from about 0.4 to about 0.6 millimeters. Preferably, the diameter of the expulsion member is less than the diameter of the tubular insertion member to allow for a telescopic arrangement of the two.

The tubular insertion member of the applicator provided by the present invention is preferably substantially closed prior to expulsion of the materials contained therein. Alternatively, the insertion end of the applicator can be more or less open, that is the diameter along the length of the tubular insertion member is substantially equivalent to the diameter of the insertion end. Procter & Gamble, of Cincinnati, Ohio, currently offers for sale an open-ended tampon applicator under the trade name TAMPAX flushable applicator tampons. One technique for substantially closing the insertion end of the applicator is by employing a plurality of inwardly curved petals. The petals will flex and/or hinge to an open position upon expelling materials contained by the applicator. The number of petals generally ranges from about 4 to about 6. An alternative technique for substantially closing the insertion end of an applicator is by pleating the insertion end. This technique is disclosed in U.S. Pat. No. 5,782,793. When an applicator is constructed with more than one layer of material, a single layer may extend into the insertion end in an effort to reduce the force required to expel the contained materials. An example of this is disclosed in U.S. Pat. No. 5,827,214. These collective closures may be of spherical shape, or alternatively tapered shape.

The applicator of the present invention can be used for the delivery of catemenial devices, such as tampons, intravaginal collection devices, and interlabial pads. The applicator may also be useful for delivery of oral, rectal, and vaginal suppositories, as well as nasal devices, such as nasal tampons. Further, the applicator can be used for delivery of various other materials including, medicaments, moisturizers, vitamins and minerals, spermicides, and odor controlling agents. These materials may be in the form of solids, creams, foams, gels, and the like.

The disclosures of all U.S. patents and patent applications, as well as any corresponding published foreign patent applications, mentioned throughout this patent application are hereby incorporated by reference herein.

The specification and embodiments above are presented to aid in the complete and non-limiting understanding of the invention disclosed herein. Since many variations and embodiments of the invention can be made without departing from its spirit and scope, the invention resides in the claims hereinafter appended.

What is claimed is:

1. A paperboard applicator for delivering materials into a mammalian body cavity, comprising: an elongate paperboard insertion member having a length extending from an insertion end to a gripper end opposite thereof, the gripper end comprising an indentation dimensioned to substantially accept a user's manual digit, said indentation comprising a first shoulder substantially adjacent the gripper end and a second shoulder disposed toward the insertion end, wherein the indentation has a perimeter that is less than the perimeter of the insertion member adjacent at least one of the first and second shoulders.

2. The applicator of claim 1 wherein the indentation has a minimum outside perimeter and the insertion member has first and second outside perimeters at the first and second shoulders, respectively, and wherein the minimum perimeter of the indentation is about 60% to about 90% of the second perimeter, the respective perimeters defined by a plane perpendicular to the length of the insertion member.

3. The applicator of claim 2 wherein the first and second perimeters are substantially dimensionally equal.

4. The applicator of claim 1 wherein the insertion member is substantially tubular.

5. The applicator of claim 4 wherein the indentation has a minimum diameter and the insertion member has first and second diameters at the first and second shoulders, respectively, and wherein the minimum diameter of the indentation is about 60% to about 90% of the second diameter.

6. The applicator of claim 5 wherein the first and second diameters are substantially equal.

7. The applciator of claim 5 wherein the indentation has a substantially constant diameter between the shoulders.

8. The applicator of claim 1 wherein the indentation has a length from about 10 to about 25 millimeters.

9. The applicator of claim 1 wherein a layer of shrinkable polymeric material resides within at least a portion of the indentation.

10. The applicator of claim 1 wherein a layer of elastomeric material resides within at least a portion of the indentation.

11. The applicator of claim 1 wherein the insertion end is substantially closed.

12. The applicator of claim 1 wherein the insertion member has an outer layer comprising polymeric material.

13. The applicator of claim 12 wherein the polymeric material is epoxy.

14. The applicator of claim 1 further comprising an elongate expulsion member which is slideably within the elongate insertion member.

15. A paperboard applicator for delivering materials into a mammalian body cavity, comprising: a paperboard tubular insertion member comprising an insertion end and a gripper end opposite thereof, the gripper end comprising an indentation, said indentation comprising a first shoulder substantially adjacent the gripper end and a second shoulder disposed toward the insertion end, the indentation having a perimeter that is less than the perimeter of the insertion member adjacent at least one of the first and second shoulders and a length sufficient to substantially accept a user's manual digit such that excess bridging by the user's digit across the indentation does not occur.

16. The applicator of claim 15 wherein the indentation has a minimum diameter and the insertion member has first and second diameters at the first and second shoulders, respectively, and wherein the minimum diameter of the indentation is about 60% to about 90% of the second diameter.

17. The applicator of claim 16 wherein the first and second diameters are substantially equal.

18. The applicator of claim 15 wherein the indentation has a length from about 10 to about 25 millimeters.

19. A paperboard applicator for delivering materials into a mammalian body cavity, comprising: an elongate insertion member comprising an insertion end and a gripper end opposite thereof, the gripper end comprising an indentation, said indentation comprising a first shoulder substantially adjacent the gripper end and a second shoulder disposed toward the insertion end, wherein the indentation has a perimeter that is less than the perimeter of the insertion member adjacent at least one of the first and second shoulders, a length of at least 10 millimeters and a length to depth ratio of from about 4 to about 25.

20. The applicator of claim 19 wherein indentation has a depth from about 1 to about 2.5 millimeters.

\* \* \* \* \*